(12) United States Patent
Shelly et al.

(10) Patent No.: US 9,044,560 B2
(45) Date of Patent: *Jun. 2, 2015

(54) SERVO VENTILATION USING PRESSURE DROP FROM BASELINE

(75) Inventors: Benjamin Irwin Shelly, Oakmont, PA (US); Michael Thomas Kane, Harrison City, PA (US); Gregory Delano Matthews, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 275 days.

This patent is subject to a terminal disclaimer.

(21) Appl. No.: 13/521,485

(22) PCT Filed: Dec. 17, 2010

(86) PCT No.: PCT/IB2010/055915
§ 371 (c)(1),
(2), (4) Date: Jul. 11, 2012

(87) PCT Pub. No.: WO2011/086434
PCT Pub. Date: Jul. 21, 2011

(65) Prior Publication Data
US 2013/0125892 A1    May 23, 2013

Related U.S. Application Data

(60) Provisional application No. 61/294,875, filed on Jan. 14, 2010.

(51) Int. Cl.
*A61M 11/00* (2006.01)
*A61M 16/00* (2006.01)
*A61M 16/06* (2006.01)
(Continued)

(52) U.S. Cl.
CPC .......... *A61M 16/0066* (2013.01); *A61M 16/00* (2013.01); *A61M 2016/0039* (2013.01); *A61M 2205/50* (2013.01); *A61M 2205/502* (2013.01); *A61M 2205/7518* (2013.01); *A61M 2209/01* (2013.01); *A61M 16/06* (2013.01); *A61M 16/0875* (2013.01); *A61M 16/20* (2013.01); *A61M 16/0009* (2014.02); *A61M 16/0069* (2014.02); *A61M 16/204* (2014.02)

(58) Field of Classification Search
None
See application file for complete search history.

(56) References Cited

U.S. PATENT DOCUMENTS 5,044,362 A    9/1991 Younes
5,107,830 A    4/1992 Younes
(Continued)

FOREIGN PATENT DOCUMENTS

EP    2008581 A2    12/2009

*Primary Examiner* — Steven Douglas
(74) *Attorney, Agent, or Firm* — Michael W. Haas

(57) ABSTRACT

A system and method for delivering a flow of breathing gas to an airway of a patient that includes a gas flow generator and a patient circuit that communicates the flow of gas to an airway of a patient. A sensor measures a characteristic associated with the flow of gas, such as flow rate. A controller determines a first characteristic based on the measured characteristic and a target of the flow of gas to be delivered to the patient. The controller controls the delivery of gas to the patient by 1) providing a baseline positive pressure support amount to the patient and 2) providing a modified pressure support amount by reducing the baseline amount by a given amount if the first characteristic is above the target. The baseline pressure includes a pressure provided during inspiration that is higher than a pressure provided during expiration.

23 Claims, 6 Drawing Sheets

(51) Int. Cl.
*A61M 16/08* (2006.01)
*A61M 16/20* (2006.01)

(56) References Cited

U.S. PATENT DOCUMENTS

| | | | |
|---|---|---|---|
| 5,148,802 A | 9/1992 | Sanders | |
| 5,203,343 A | 4/1993 | Axe | |
| 5,313,937 A | 5/1994 | Zdrojkowski | |
| 5,433,193 A | 7/1995 | Sanders | |
| 5,458,137 A | 10/1995 | Axe | |
| 5,535,738 A | 7/1996 | Estes | |
| 5,598,838 A | 2/1997 | Servidio | |
| 5,632,269 A | 5/1997 | Zdrojkowski | |
| 5,645,053 A | 7/1997 | Remmers | |
| 5,697,364 A | 12/1997 | Chua | |
| 5,794,615 A | 8/1998 | Estes | |
| 5,803,065 A | 9/1998 | Zdrojkowski | |
| 5,918,597 A | 7/1999 | Jones | |
| 5,927,274 A | 7/1999 | Servidio | |
| 6,029,664 A | 2/2000 | Zdrojkowski | |
| 6,087,747 A | 7/2000 | Dhuler | |
| 6,105,575 A | 8/2000 | Estes | |
| 6,532,959 B1 | 3/2003 | Berthon-Jones | |
| 6,532,960 B1 | 3/2003 | Yurko | |
| 6,539,940 B2 | 4/2003 | Zdrojkowski | |
| 6,609,517 B1 | 8/2003 | Estes | |
| 6,626,175 B2 | 9/2003 | Jafari | |
| 6,640,806 B2 | 11/2003 | Yurko | |
| 6,752,151 B2 * | 6/2004 | Hill | 128/204.18 |
| 6,951,217 B2 | 10/2005 | Berthon-Jones | |
| 7,011,091 B2 | 3/2006 | Hill | |
| 7,168,429 B2 | 1/2007 | Matthews | |
| 7,267,122 B2 | 9/2007 | Hill | |
| 7,662,101 B2 * | 2/2010 | Lee et al. | 600/484 |
| 7,717,110 B2 | 5/2010 | Kane | |
| 8,220,456 B2 * | 7/2012 | Kane et al. | 128/204.23 |
| 8,695,595 B2 * | 4/2014 | Kane et al. | 128/204.23 |
| 2003/0121519 A1 | 7/2003 | Estes | |
| 2004/0237963 A1 | 12/2004 | Berthon-Jones | |
| 2005/0065567 A1 | 3/2005 | Lee | |
| 2005/0076908 A1 * | 4/2005 | Lee et al. | 128/204.23 |
| 2005/0268913 A1 | 12/2005 | Morris | |
| 2006/0070624 A1 | 4/2006 | Kane | |
| 2007/0221224 A1 | 9/2007 | Pittman | |
| 2009/0266360 A1 * | 10/2009 | Acker et al. | 128/204.21 |
| 2010/0186743 A1 * | 7/2010 | Kane et al. | 128/204.23 |
| 2013/0047990 A1 * | 2/2013 | Shelly et al. | 128/204.23 |
| 2014/0109910 A1 * | 4/2014 | Colbaugh | 128/204.23 |

* cited by examiner

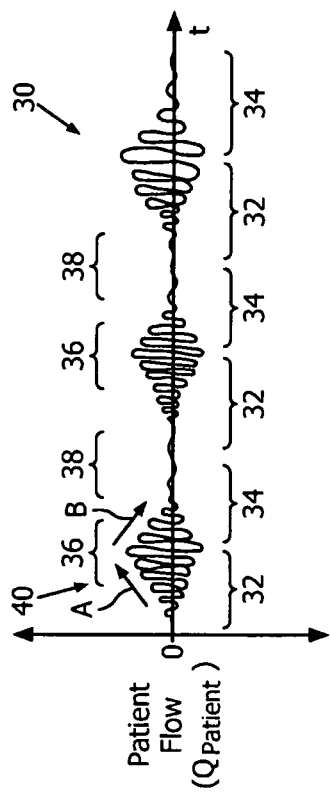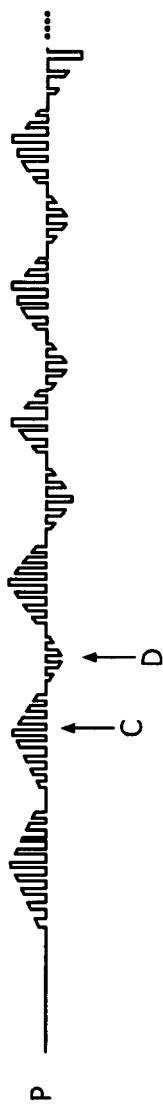
FIG. 1
FIG. 2A
FIG. 2B

SERVO VENTILATION USING PRESSURE DROP FROM BASELINE

CROSS-REFERENCE TO RELATED APPLICATIONS

This patent application claims the priority benefit under 35 U.S.C. §371 of international patent application no. PCT/IB2010/055915, filed Dec. 17, 2010, which claims the priority benefit under 35 U.S.C. §119(e) of U.S. Provisional Application No. 61/294,875 filed on Jan. 14, 2010, the contents of which are herein incorporated by reference.

BACKGROUND OF THE INVENTION

1. Field of the Disclosure

The invention relates generally to a method and apparatus for providing a pressure therapy particularly suited to treat Cheyne-Stokes respiration and other breathing disorders commonly associated with congestive heart failure.

2. Description of the Related Art

Congestive heart failure (CHF) patients commonly suffer from respiratory disorders, such as obstructive sleep apnea (OSA) or central apneas. Another such respiratory disorder CHF patients often experience during sleep is known as Cheyne-Stokes respiration. FIG. 1 illustrates a typical Cheyne-Stokes respiration (CSR) pattern 30, which is characterized by rhythmic waxing periods 32 and waning periods 34 of respiration, with regularly recurring periods of high respiratory drive (hyperpnea) 36 and low respiratory drive (hypopnea or apnea) 38. A typical Cheyne-Stokes cycle, generally indicated at 40, lasts about one minute and is characterized by a crescendo (arrow A), in which the peak respiratory flow of the patient increases over several breath cycles, and decrescendo (arrow B), in which the peak respiratory flow of the patient decreases over several breath cycles. The typical Cheyne-Stokes cycle ends with a central apnea or hypopnea following the decrescendo phase. Apneas, hyperpneas, and the abnormal change in the depth and rate of breathing often cause arousals and, thus, degrade sleep quality. This disruption in sleep, as well as the periodic desaturation of arterial oxygen, caused by the CSR cycle stresses the cardiovascular system and specifically the heart.

The earliest treatment for CSR involved stimulating the respiratory drive by administering Theophyline, caffeine, or 1-3% inspired carbon dioxide to the patient. Although sometimes effective in reducing CSR, the downside of these treatments, which increase the respiratory rate, is that the increase in respiratory rate proportionally increases cardiac and respiratory workload.

Recent work in the treatment of sleep apnea and related breathing disorders has included bi-level positive airway therapy. In bi-level therapy, pressure is applied alternately at relatively higher and lower prescription pressure levels within the airway of the patient so that the therapeutic air pressure is alternately administered at a larger and smaller magnitude. The higher and lower magnitude positive prescription pressure levels are known as inspiratory positive airway pressure (IPAP) and expiratory positive airway pressure (EPAP), respectively. The inspiratory and expiratory pressure are synchronized with the patient's inspiratory cycle and expiratory cycle, respectively.

Some preliminary investigations reveal that cardiac output improves when patients are supported using bi-level pressure therapy. It has also been recognized that CSR can be treated by augmenting respiratory effort with positive pressure support when the CSR pattern is in hypopnea region 38. To accomplish this, it is known to use a ventilator or pressure support system to deliver machine triggered breaths during the hypopnea interval when the patient's own respiratory drive is reduced or not present. In addition, ventilatory efficiency may be decreased when flow is in a hyperpnea region 36. Alternatively, another method of treating CSR is where $CO_2$ is selectively rebreathed during the hyperneic phase of the CSR cycle. However, this method requires additional equipment to be used with the typical ventilator system.

SUMMARY OF THE INVENTION

One aspect provides a system for delivering a flow of breathing gas to an airway of a patient. The system includes a gas flow generator that generates a flow of gas and a patient circuit coupled to the gas flow generator and adapted to communicate the flow of gas to an airway of the patient. The system also includes a sensor associated with the gas flow generator or the patient circuit and adapted to monitor a characteristic associated with the flow of gas, such as the flow rate. The system further includes a controller that determines a first characteristic based on the monitored gas flow characteristic and a target of the flow of gas to be delivered to the patient. The controller controls the delivery of the flow of gas to the airway of the patient from the gas flow generator via the patient circuit by 1) providing a baseline positive pressure support amount to the patient and 2) providing a modified pressure support amount to the patient by reducing the baseline positive pressure support amount by a reducing pressure support amount if the first characteristic is above the target. The baseline positive pressure support amount comprises a pressure provided to the patient during inspiration that is higher than a pressure provided to the patient during expiration.

Another aspect provides a method of ventilating a patient including delivering a flow of gas to the airway of a patient from a source of breathing gas via a patient circuit. The method also includes measuring a characteristic associated with the flow of gas, determining a first characteristic based on the measured characteristic and determining a target of the flow of gas to be delivered to the patient. The method further includes controlling the delivery of the flow of gas to the airway of the patient from the gas flow generator via the patient circuit by 1) providing a baseline positive pressure support amount to the patient and 2) providing a modified pressure support amount to the patient by reducing the baseline positive pressure support amount by a reduced pressure support amount if the first characteristic is above the target. The baseline positive pressure support amount comprises a pressure provided to the patient during inspiration that is higher than a pressure provided to the patient during expiration.

Another aspect provides a system for ventilating a patient including means for delivering a flow of gas to the airway of a patient from a source of breathing gas via a patient circuit. The method also includes means for determining a target of the flow of gas to be delivered to the patient. The method further includes means for controlling the delivery of the flow of gas to the airway of the patient from the gas flow generator via the patient circuit by 1) providing a baseline positive pressure support amount to the patient and 2) providing a modified pressure support amount to the patient by reducing the baseline positive pressure support amount by a reduced pressure support amount if a first characteristic first determined based on a monitored gas flow characteristic is above the target. The baseline positive pressure support amount comprises a pressure provided to the patient during inspiration that is higher than a pressure provided to the patient during expiration.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein can be considered drawn to scale. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 1 illustrates a typical Cheyne-Stokes respiratory cycle that is treated by the pressure support system of the present invention;

FIGS. 2A and 2B illustrate waveforms of the patient flow and waveforms of the pressure being delivered to the patient, respectively, in accordance with an embodiment;

DETAILED DESCRIPTION OF EXEMPLARY EMBODIMENTS

FIG. 2A illustrates waveform, i.e., a graph of the measure rate of flow of gas at the airway of the patient, and FIG. 2B illustrates waveform of pressure support delivered to the patient by a pressure support system 10 (see FIG. 3) in accordance with an embodiment. System 10 may use these patient flow values to obtain other measures of patient flow, such as, for example, peak flow, minute ventilation, tidal volume, average inspiratory flow, or other measures. Initially, as indicated by arrow C in FIG. 2B, the patient experiences a CSR event. During the hyperneic phase of the CSR pattern, negative pressure support is enabled and delivered to the patient, as indicated by arrow D. Positive pressure support and negative pressure support may be applied until the CSR events have been reduced or eliminated. Positive pressure support as used herein is where the inspiratory pressure level, such as the IPAP, is higher than the expiratory pressure level, such as the EPAP. In contrast, the negative pressure support as used herein is where the inspiratory pressure level is lower than the expiratory pressure level. Negative pressure support may be provided when both the inspiratory and expiratory pressures are above atmospheric pressure, or when either pressure is at or below atmospheric pressure. Thus, to provide negative pressure support, the inspiratory pressure level may be decreased or the expiratory level may be increased so that inspiratory pressure level is lower than the expiratory pressure level. Negative pressure support may be undesirable, uncomfortable, and unnecessary when the patient is awake or aroused from sleep. Therefore, in some embodiments, system 10 monitors for the waxing-waning pattern of CSR to ensure that CSR is occurring before enabling negative pressure support.

The pressure support amount or level is the difference between the inspiratory pressure and the expiratory pressure. In some embodiments, system 10 may provide a fixed amount of normal or baseline positive pressure support during inspiration. That is, by default, system 10 may provide an inspiratory pressure amount or level that is higher than the expiratory pressure amount or level. In some embodiments, the amount of baseline pressure support may be 15 cm $H_2O$. The pressure support may be modified when certain events occur, such as, for example, when CSR is detected and the measure of flow is above a target. The pressure support may be modified by reducing the baseline positive pressure support amount by a negative pressure support amount. In some embodiments, the pressure support may also be modified by adding a positive pressure support amount to the baseline pressure support amount.

Figure 3:
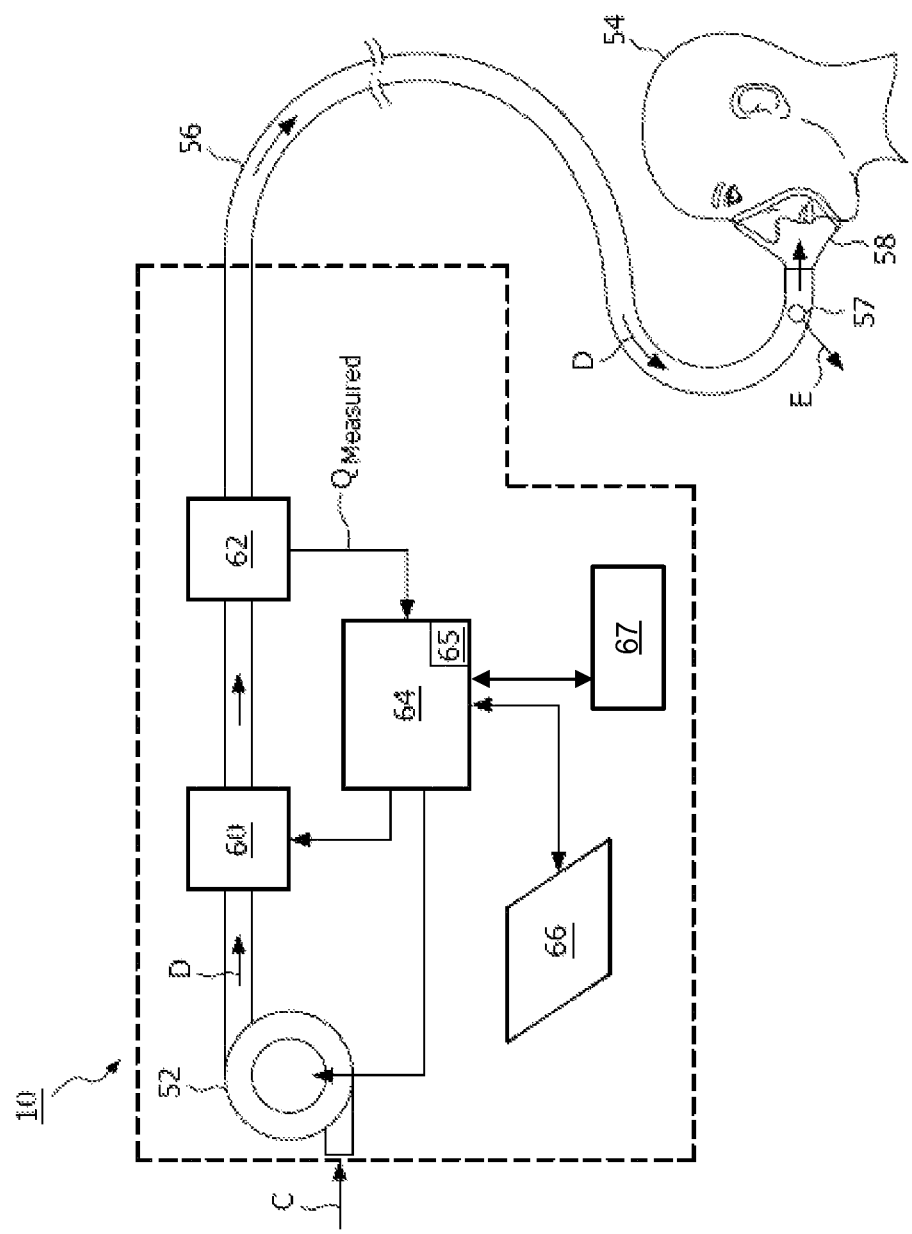
FIG. 3 is a functional block diagram of a positive airway pressure support system adapted to implement the pressure support therapy according to the principles of the present invention.

FIG. 3 schematically illustrates an airway pressure support system 10 suitable for providing an improved variable positive airway pressure mode of pressure support to a patient according to the principles of the present invention. This mode of pressure support is particularly suited to treat Cheyne-Stokes respiration. Pressure support system 10 includes a gas flow/pressure generator 52, such as a blower used in a conventional CPAP or bi-level pressure support device, piston, bellows, compressor, or any other device that receives breathing gas, generally indicated by arrow C, from any suitable source, e.g., a pressurized tank of oxygen or air, the ambient atmosphere, or a combination thereof. Gas flow/pressure generator 52 generates a flow of breathing gas, such as air, oxygen, or a mixture thereof, for delivery to an airway of a patient 54 at relatively higher and lower pressures. System 10 may also include devices or components to provide breathing gas at a pressure that is below atmospheric. That is, in some embodiments, the system may include two blowers and a valve configured to provide breathing gas at a pressure that is below atmospheric.

The pressurized flow of breathing gas, generally indicated by arrow D from gas flow/pressure generator 52 is delivered, via a delivery conduit 56, to a breathing mask or patient interface 58 of any known construction, which is typically worn by or otherwise attached to a patient 54 to communicate the flow of breathing gas to the airway of the patient. Delivery conduit 56 and patient interface device 58 are typically collectively referred to as a patient circuit.

In one embodiment, the variable positive airway pressure support system essentially functions as a bi-level pressure support system, and, therefore, includes all of the capabilities necessary in such systems in order to provide separate inspiratory pressure and expiratory pressure levels to the patient. This includes receiving the necessary parameters via input commands, signals, instructions or information for providing a bi-level pressure, such as maximum and minimum inspiratory and expiratory pressure settings. The flow signal $Q_{measured}$ from flow sensor 62 is also provided to the pressure support process, which controls the pressure controller to output the desired inspiratory and expiratory waveforms. Typically, carrying out the pressure support operation includes estimating or determining the actual patient flow $Q_{patient}$ based on the flow signal $Q_{measured}$, determining whether the patient is in the inspiratory or expiratory phase of the respiratory cycle and providing an I/E state signal indicative of the respiratory state of the patient, and triggering and cycling the pressure support system 10.

Pressure support system 10 shown in FIG. 3 is a single-limb system, meaning that the patient circuit includes only a delivery conduit 56 connecting the patient to the pressure support device. As such, an exhaust vent 57 is provided in the delivery conduit for venting exhaled gases from the system as indicated by arrow E. It should be noted that the exhaust vent can be provided at other locations in addition to or instead of in the delivery conduit, such as in the patient interface device. It should also be understood that the exhaust vent can have a wide variety of configurations depending on the desired manner in which gas is to be vented from the pressure support system 10.

Pressure support system 10 may optionally be a two-limb system, having a delivery conduit and an exhaust conduit connected to the patient.

In the illustrated embodiment of the present invention, patient interface 58 is a nasal/oral mask. It is to be understood, however, that patient interface 58 can include a nasal mask, nasal pillows, tracheal tube, endotracheal tube, or any other device that provides the gas flow communicating function. Also, as used herein, the phrase "patient interface" can include delivery conduit 56 and any other structures that connect the source of pressurized breathing gas to the patient.

It is to be understood that various components may be provided in or coupled to the patient circuit. For example, a bacteria filter, pressure control valve, flow control valve, sensor, meter, pressure filter, humidifier and/or heater can be provided in or attached to the patient circuit. Likewise, other components, such as muffler and filters can be provided at the inlet of gas flow/pressure generator 52 and at the outlet of valve 60.

In the illustrated embodiment, variable positive airway pressure support system 10 includes a pressure controller. In one embodiment, the pressure controller can take the form of a control valve 60 provided in delivery conduit 56. Valve 60 controls the pressure of the flow of breathing gas from gas flow/pressure generator 52 delivered to the patient. For present purposes, gas flow/pressure generator 52 and valve 60 are collectively referred to as a "pressure generating system" because they act in concert to control the pressure and/or flow of gas delivered to the patient.

It should be apparent that other techniques for controlling the pressure delivered to the patient by the gas flow/pressure generator, such as varying the blower speed, either alone or in combination with a pressure control valve may be used. Thus, valve 60 is optional depending on the technique used to control the pressure of the flow of breathing gas delivered to the patient. If valve 60 is eliminated, the pressure generating system may correspond to gas flow/pressure generator 52 alone, and the pressure of gas in the patient circuit is controlled, for example, by controlling the motor speed of the gas flow/pressure generator.

Pressure support system 10 further includes a sensor 62 that measures a characteristic associated with the flow of gas within delivery conduit 56. In an exemplary embodiment, sensor 62 is a flow sensor that measures a rate of flow of gas within the delivery conduit. Sensor 62 can be any conventional flow sensor, such a pressure drop based flow sensor, ultrasonic flow sensor, or any other sensor capable of monitoring or measuring the rate of flow of gas within delivery conduit. In accordance with an embodiment shown in FIG. 3, flow sensor 62 is interposed in line with delivery conduit 56, such as downstream of valve 60. Flow sensor 62 generates a flow signal $Q_{measured}$ that is provided to a controller 64 and is used by the controller to determine the flow of gas at the patient $Q_{patient}$.

Techniques for calculating $Q_{patient}$ based on $Q_{measured}$ are well known, and take into consideration the pressure drop of the patient circuit, known leaks from the system, i.e., the intentional exhausting of gas from the circuit as indicated by arrow E in FIG. 3, and unknown leaks from the system, such a leaks at the mask/patient interface. Any conventional technique for calculating leak flow may be used, and this calculation may be used in calculating $Q_{patient}$ based on $Q_{measured}$. Examples of such techniques are taught by U.S. Pat. Nos. 5,148,802; 5,313,937; 5,433,193; 5,632,269; 5,803,065; 6,029,664; 6,539,940; 6,626,175, and 7,011,091, the contents of each of which are incorporated by reference into the present invention.

Other techniques for measuring the patient flow of the patient may be used. For example, the flow can be measured directly at the patient, in which case the measured flow corresponds directly the patient flow $Q_{patient}$ and no flow estimation is necessary. It is also contemplated that flow may be measured at other locations along delivery conduit 56.

In addition, the estimated patient flow $Q_{patient}$ may be determined based on other characteristics of the pressure support system 10. For example, the operation of the gas flow/pressure generator or a flow/pressure controller, such as a valve, is affected by the flow in the patient circuit, or by the systems attempt to maintain the pressure in the system. As a result, monitoring a characteristic of the system, such as monitoring the power, torque, and/or rotating speed of the pressure generator or the position of the valve, can be used as a surrogate for measuring the patient flow directly. It is also known to measure patient flow using a flow sensor upstream of the gas flow/pressure generator. Any combination of such flow measuring techniques can also be used. In these latter cases, an estimation of patient flow $Q_{patient}$ based on the measured flow or other parameter will be needed.

An input/output device 66 is provided for setting various parameters used by the variable positive airway pressure support system 10, as well as for displaying and outputting information and data to a user, such as a clinician or caregiver. Input/output terminals may optionally be provided so that the operation information and data collected by the pressure support system 10 can be monitored and controlled remotely. Controller 64 may be or include a microprocessor that is/are capable of implementing and executing routines for monitoring characteristics of patient respiration and controlling the flow of breathing gas based thereon as discussed in detail below. In addition, in one embodiment, controller 64 includes memory, or memory arrays 65 for storing and buffering information necessary to implement the techniques discussed herein. It is to be understood, that controller 64 can be a single processing component, or can be comprised of multiple components (memories, processor, arrays, logic circuits, etc.) operating in conjunction to implement the techniques discussed herein.

In an embodiment, controller 64 controls gas flow/pressure generator 52, valve 60, or both to deliver a pressure waveform to an airway of patient 54. In an embodiment, the pressure waveform is essentially a bi-level pressure waveform that alternates between an inspiratory pressure level and an expiratory pressure level (see FIGS. 4A and 4B). In some embodiments, the inspiratory pressure level is variable under the direction of controller 64 as discussed below. The maximum and minimum inspiratory pressure levels, such as the (IPAP$_{max}$, IPAP$_{min}$, are provided to the controller via input device 66 from a user. Alternatively or additionally, the expiratory pressure level is variable under the direction of controller 64 (see FIGS. 4A and 4B). In such embodiments, the maximum and minimum expiratory pressure levels, such as the (EPAP$_{max}$, EPAP$_{min}$), are provided to the controller via input device 66 from a user. It should be understood that the maximum and minimum inspiratory/expiratory levels can also be pre-established and stored in the controller as a default or in lieu of input parameters from the system operator.

Figure 4A:
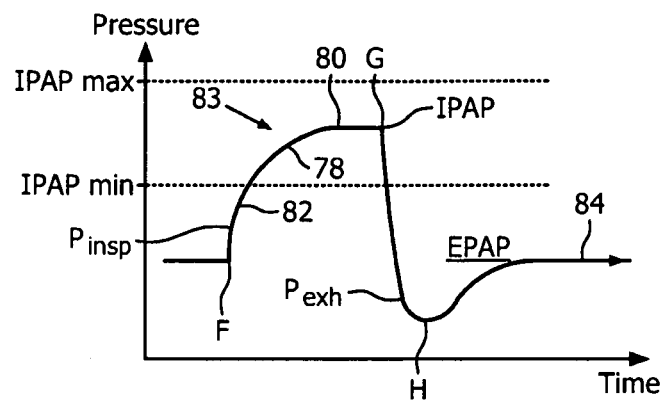
FIGS. 4A and 4B illustrate exemplary pressure waveforms delivered by the pressure support system of FIG. 3 in accordance with an embodiment.
Figure 4B:
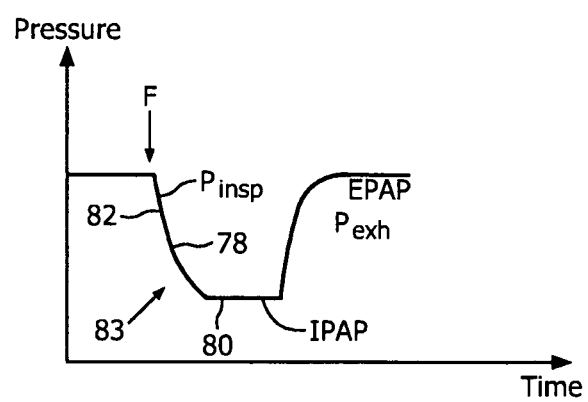

FIGS. 4A and 4B illustrate exemplary pressure waveform 78 that can be provided by the pressure support system 10 to treat CSR. As shown in FIG. 4A and/or 4B, at time F, which is the trigger point from expiration to inspiration, the patient begins inspiring and triggers the pressure support system 10 to transition to an inspiratory pressure level 80. The shape and duration of the pressure increase or rise 82 from trigger point F to the inspiratory pressure level can be fixed or variable, as taught for example, in U.S. Pat. Nos. 5,598,838; 5,927,274; 6,532,960; and 6,640,806, the contents of each of which are incorporated herein by reference. In the illustrated embodiment, the shape of the pressure increase is exponential. It is to be understood that other shapes, such as step functions or linear ramps are contemplated for the pressure rise portion of an inspiratory portion 83 of the pressure waveform.

It should be further understood that the present invention contemplates that an inspiratory portion 83 and the expiratory portion P$_{exh}$ of pressure waveform 78 can have a variety of configurations. That is, the pressure waveform during inspiration P$_{insp}$ and/or the expiratory portion P$_{exh}$ can be controlled using conventional pressure support or ventilation techniques, such as proportional assist ventilation (PAV®), which is described in U.S. Pat. Nos. 5,044,362 and 5,107,830, or proportional positive airway pressure (PPAP), which is described in U.S. Pat. Nos. 5,535,738; 5,794,615; 6,105,575; and 6,609,517 ("the PPAP patents") the contents of each of which are incorporated herein by reference. According to the PPAP patents, the waveform for inspiratory pressure, P$_{insp}$, output by the pressure support system 10 during the inspiratory phase of the breathing cycle may be determined according to the following equation:

$$P_{insp} = IPAP + Gain_{insp} * Q_{patient} \quad 1.1$$

where Gain$_{insp}$ is a gain factor, typically selected by a caregiver. Gain$_{insp}$ can be set to any value including a value of one (1).

The expiratory pressure, P$_{exh}$, output by the pressure support system 10 during the expiratory phase of the breathing cycle may be determined according to the following equation:

$$P_{exh} = EPAP + Gain_{exh} * Q_{patient} \quad 1.2$$

where Gain$_{exh}$ is a gain factor, typically selected by a caregiver. Gain$_{exh}$ can be set to any value including a value of one (1).

It should be noted that for present purposes, flow into the patient is considered positive flow, and flow out of the patient is considered negative flow. Thus, the value of the patient flow Q$_{patient}$ is taken at the patient's airway. The flow measured at a location distal from the patient Q$_{measured}$ may have a positive offset due, for example, to exhausting of gas from the circuit, which is factored out by leak estimation techniques.

Controller 64 receives flow Q$_{measured}$ from flow sensor 62 and implements equations 1.1, 1.2, or both, for generating the inspiratory pressure waveform P$_{insp}$ and expiratory pressure waveform P$_{exh}$.

Figure 5:
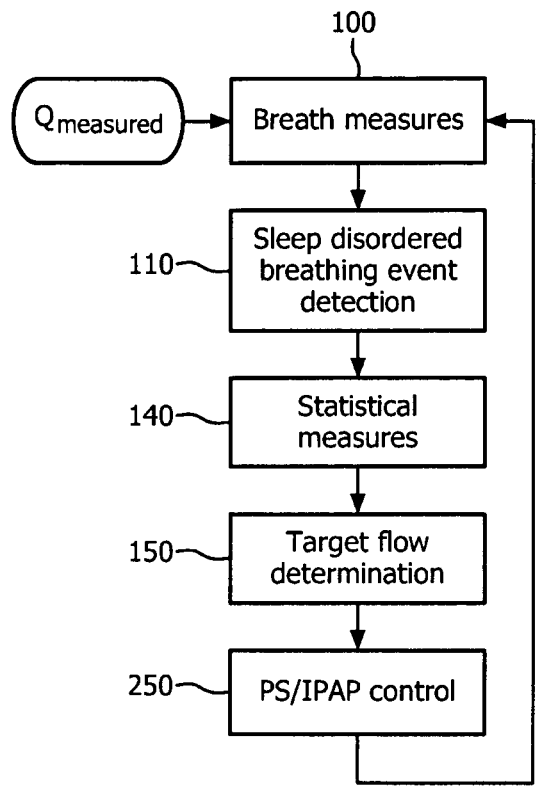
FIG. 5 is a flowchart illustrating a portion of the process for implementing the pressure support mode of the present invention.

Controller 64 implements an algorithm to control the pressure of the flow of gas delivered to the patient. The process shown in FIG. 5 shows the algorithm performed by the pressure support system 10 during each breath. As shown in FIG. 5, a primary input to this algorithm is the output of flow sensor 62 (Q$_{measured}$) The output is sampled at a sampling rate, such as 100 samples/second, to produce a new estimated patient flow Q$_{patient}$ determination every 10 milliseconds. Q$_{patient}$ may be calculated based on Q$_{measured}$ using known flow/leak estimation techniques. Q$_{patient}$ can also be measured directly at the mask so that flow estimation is not needed. The measured flow Q$_{measured}$ may optionally be used directly for the calculations of the present invention, recognizing that the measured flow is not an accurate representation of the flow at the airway of the patient.

A history of the patient flow Q$_{patient}$ or a measure of the patient flow is stored in memory to perform the flow analysis discussed below. Controller 64 includes storage arrays and buffers to calculate parameters in real-time, and store the results in moving windows.

According to one aspect of the present invention, controller 64 monitors the patient flow to determine the transitions from inspiration to expiration and from expiration to inspiration. Any suitable techniques may be used, such as using both volume and wave shape to (a) trigger the device to provide the inspiratory pressure P$_{insp}$ and (b) cycle the device to provide the expiratory pressure P$_{exh}$, which are described in U.S. Pat. Nos. 5,148,802; 5,313,937; 5,433,193; 5,632,269; 6,029,664; 6,539,940; and 6,626,175.

FIG. 5 is a flow chart illustrating a portion of the process for implementing the pressure support mode of the present invention. As mentioned above, a baseline positive pressure support is provided to the patient during inspiration. It is contemplated that the baseline positive pressure support may be predetermined and programmed into the controller, or may be set by the patient. The amount of pressure support provided to the patient may be modified according to the following steps. In step 100, in some embodiments, the controller analyzes the patient's instantaneous flow Q$_{patient}$ to produce measures (i.e., a characteristic) of flow. In one embodiment, Q$_{patient}$ is used to calculate the instantaneous average inspiratory flow (Q$_{ave}$(t)) and maximum instantaneous average inspiratory flow (Q$_{ave}$(max)), which are continuously calculated during the inspiratory phase of the respiratory cycle. The instantaneous average inspiratory flow is the summation of positive, i.e., inspiratory, patient flows over a period of time divided by the number of samples taken during that period of time. The Maximum Average Inspiratory Flow (Q$_{ave}$ (max)) is the maximum value of the Instantaneous Average Inspiratory Flow over one breath, i.e., during the inspiratory phase of the respiratory cycle. It can thus be appreciated that during one given inspiratory phase of a patient's respiratory cycle, a continuum of Q$_{ave}$(t) is calculated over the entire inspiratory phase, and only one Q$_{ave}$(max) is found. In another embodiment, Q$_{patient}$ is used to calculate the Tidal Volume, Minute Ventilation, or any other measures of flow.

As mentioned above, Cheyne-Stokes respiration (CSR) pattern 30 is characterized by rhythmic waxing periods 32 and waning periods 34 of respiration, with regularly recurring periods of high respiratory drive (hyperpnea) 36 and low respiratory drive (hypopnea or apnea) 38. The present invention monitors for CSR to ensure that the pressure therapy being applied to the patient is sufficient to treat CSR. Naturally, the presence of CSR indicates that the therapy is not effective. Thus, it is important that CSR events be detected accurately and monitored. The steps to detect CSR may be implemented in software run by the processor in the pressure support system 10. The present invention contemplates and those skilled in the art would appreciate that any suitable CSR detection technique can be used to monitor the effectiveness in the CSR treatment delivered to the patient. For example, CSR may be detected by monitoring the measure of flow and using the CSR Index and Flow Ratio values, as described in U.S. patent application Ser. No. 11/235,520, which is incorporated herein in its entirety. CSR may also be detected by monitoring the oxygen saturation of the user, which may be monitored using a pulse oximeter or other type of oxygen saturation monitor 67 (FIG. 3). An increase in the oxygen saturation may coincide with the waxing period of the CSR pattern, and a decrease in the oxygen saturation level may coincide with the waning period at the end of the CSR cycle. Thus, the oxygen saturation level may be monitored by the oxygen saturation monitor 67 to identify the ascending and descending states that indicate that the patient has experienced a CSR cycle. The controller 64 may obtain output of the oxygen saturation monitor 67.

In some embodiments, CSR may also be detected by comparing the peak flow for the current breath ($Q_{peak}(k)$) with the peak flow for the immediately preceding breath cycle ($Q_{peak}(k-1)$) to determine the presence of CSR, as described in U.S. Pat. No. 7,267,122, which is incorporated herein in its entirety. In such embodiments, system 10 may look for patterns comprising upward trends (crescendos), peak flow peaks (hyperpnea), downward trends (decrescendo), and peak flow valleys (hypopnea or apnea).

Any conventional technique may be used for detecting apneas and hypopneas. In its most basic form, apnea and hypopnea detection involves monitoring the patient flow $Q_{patient}$ for reductions in flow below a threshold level for a predetermined period of time. The threshold level and predetermined periods of time are levels deemed to constitute an apnea or hypopnea, i.e., meet the definition of an apnea or hypopnea.

In one embodiment, as shown in FIG. 5, the apnea and hypopnea detection techniques taught by published U.S. patent application. No. US-2003-0111079-A1 ("the '079 application") are used in step 110. The contents of the '079 application are incorporated herein by reference. In some embodiments, the weighted peak flow $Q_{wpeak}$ or the peak to peak flow of the previous breath may be used during apnea and hypopnea detection.

Periodic breathing events may also be detected using any conventional techniques. In embodiments where the maximum average inspiratory flow $Q_{ave}(max)$ is used as the measure of flow, a periodic breathing event is declared if a patient is deemed to have too much irregularity in the $Q_{ave}(max)$. Such method for detecting a periodic breathing event is described in U.S. patent application Ser. No. 11/235,520, which is incorporated herein in its entirety.

Figure 6:
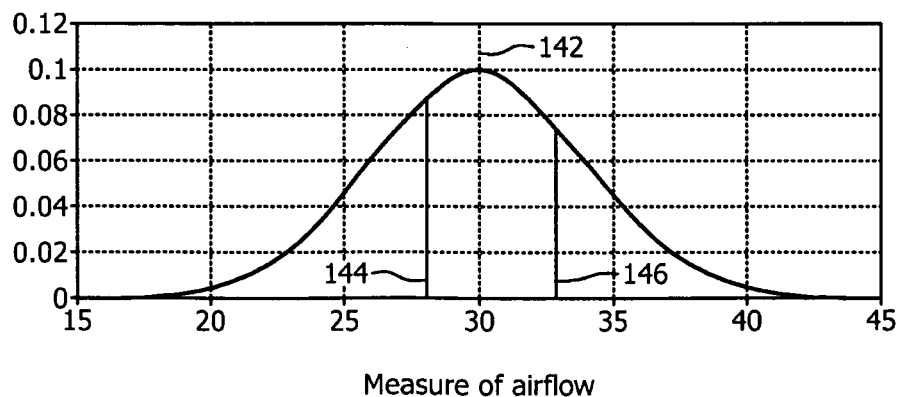
FIG. 6 is an example of a normal distribution curve for an array of Maximum Average Inspiratory Flows.

Referring back to FIG. 5, the algorithm uses statistical functions in step 140 to determine a level of ventilation which has been demonstrated by the patient over the last several minutes of breathing. The following statistical measures based on the measure of flow may be calculated by controller 64 in step 140:

1) Mean,
2) 60th percentile,
3) 95% of mean,
4) Standard Deviation, and
5) Standard Mean For example, in an embodiment that uses $Q_{ave}(max)$ as the measure of flow, FIG. 6 illustrates an exemplary normal distribution of values for $Q_{ave}(max)$ around a mean 142 having a value of 30 with a standard deviation of 4. In this example, 95% of the mean is 28.5 lpm and is indicated by line 144. The 60th percentile of the data is 33.2 lpm and is indicated by line 146. Standard Mean is the ratio of Standard Deviation over the mean expressed as a percentage. Other measures of flow may optionally be used instead of the $Q_{ave}(max)$ value, such as the mean flow, minute ventilation, peak flow, tidal volume, or other measures.

Referring back to FIG. 5, the algorithm in step 150 determines a Target value that is used in determining the amount of modified pressure support to be delivered to the patient by the pressure support system 10. The Target is a value against which a current measure of flow is compared to determine whether the baseline pressure support needs to be modified. There may optionally be a single target, dual targets, or multiple targets.

Figure 7:
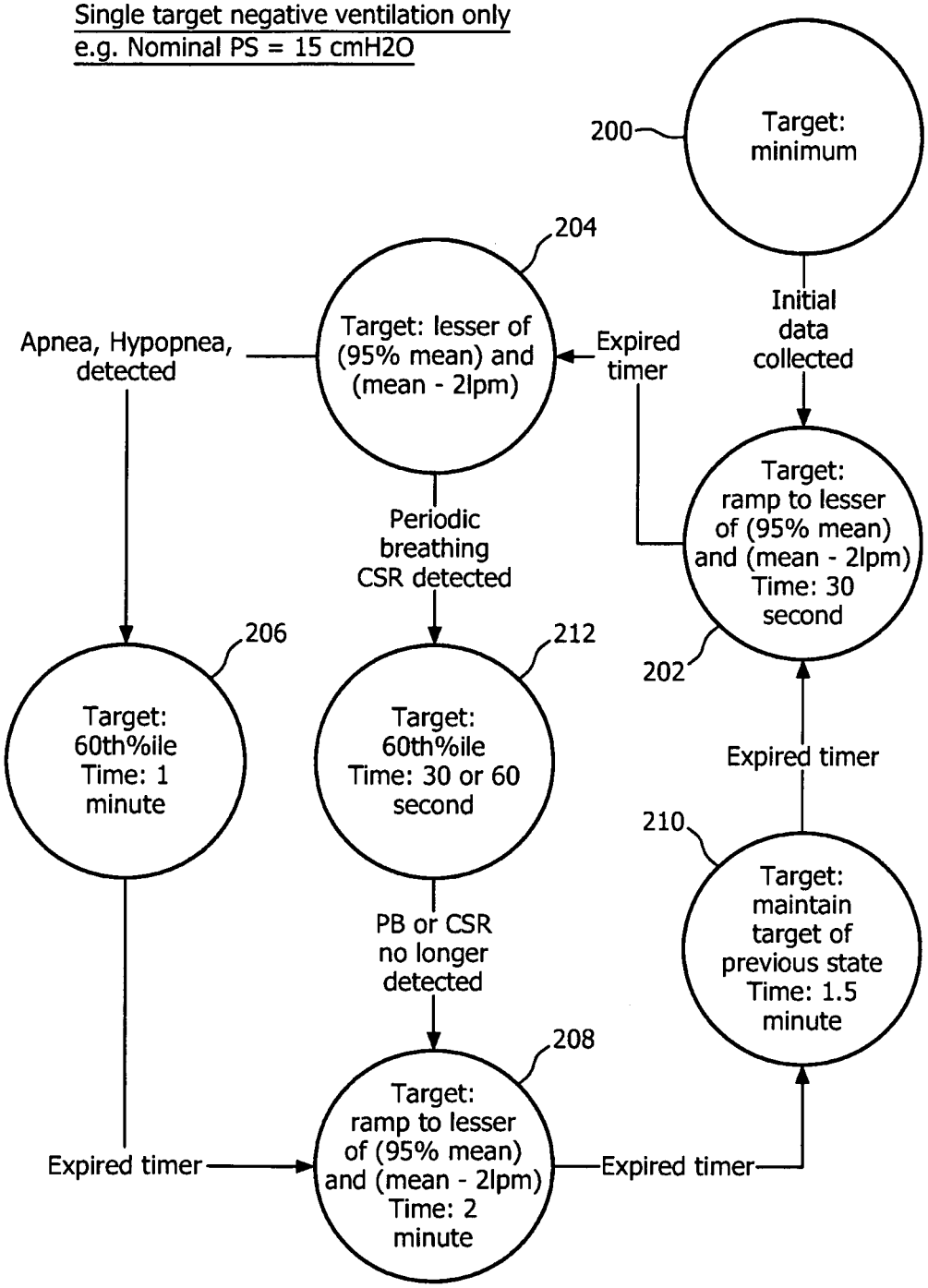
FIG. 7 is a state diagram explaining the single Target selection process in accordance with an embodiment.

FIG. 7 is a state diagram showing, in detail, the process for selecting the statistical measure to be used as the Target. When the pressure support system 10 is actuated, the Target selection process starts at step 200, where the Target is set to a minimum value and initial data is collected. In an embodiment, the minimum value for the Target is determined empirically. In the present embodiment, this minimum Target is set to 15 lpm. It is to be understood, however, that the present invention contemplates that the Target can be set by the system based on monitored physiological characteristics of the patient, such as whether the patient is deemed to be experiencing sleep disordered breathing, flow limitations, etc.

In step 202, the Target is increased to (1) a value that corresponds to a predetermined percent (e.g., 95%) of the mean value of the measure of flow data thus collected or to (2) a value that corresponds to the mean value of the measure of flow minus a fixed flow rate, which ever is smaller. In an embodiment, this fixed flow rate is 2 lpm. In an embodiment, the increase in the Target is done in a linear, ramp fashion over a period of time that spans several respiratory cycles, such as 30 seconds. This ramp in the Target is done to avoid rapid pressure fluctuations being introduced to the patient, thereby optimizing patient comfort and compliance with the treatment. The shape or pattern for the change (ramp) in the Target can be done at a fixed rate, so that the ramp is linear. It can also be done at non-linear rates, so that the ramp shape is not linear. In an embodiment, ramp in Target takes place at a rate of 0.5 lpm per breath.

In step 204, the Target value is maintained at (1) a value that corresponds to a predetermined percent (e.g., 95%) of the mean value of the measure of flow or at (2) a value that corresponds to the mean value of measure of flow minus a fixed flow rate, which ever is smaller. In an embodiment, this fixed flow rate is 2 lpm, so that the Target is maintained at the predetermined percent of measure of flow or at the mean value of (measure of flow-2 lpm), whichever is smaller. If, however, a sleep disordered breathing event, such as an apnea or hypopnea, is detected the process moves to step 206, where the Target is changed to the 60th percentile. This increase in the Target provides a greater likelihood that the system will increase the pressure support, and, thus treat the sleep disordered breathing event, than if the Target is not changed. The Target is maintained at this level for a period of time, such as one minute. After that, the process moves to step 208.

In step 208, the Target is changed back to the lesser of a 1) predetermined percent (e.g., 95%) of the mean value of the measure of flow data currently collected or 2) the mean value of measure of flow minus a fixed flow rate, such as 2 lpm. In an embodiment, this change takes place in a linear, ramp fashion, over a period of time that spans several respiratory cycles, such as 2 minutes at a rate of 0.5 lpm per breath. The change in Target can also be done at a non-linear rate.

The system maintains the Target at its current value in a hold state in step 210. This is done to allow the patient to stabilize under the new value for the Target. This prevents the system of the present invention from overcompensating or being too aggressive in its reactions to the monitored condition of the patient. In an embodiment, this hold state lasts for 1.5 minutes. Other periods of time may optionally be used, and this period of time can be selected dynamically by the system. After the 1.5 minute hold, the process returns to step 202.

If a CSR event or periodic breathing is detected during step 204, the process moves to step 212, where the Target is changed to the 60th percentile. The Target is maintained at this level for a relatively short period of time, such as 30 seconds. If no CSR events are detected during this 30 second window, the process moves to step 208. If CSR is still detected, the timer is reset. The process proceeds to step 208 when periodic breathing or CSR is no longer detected and the 30 seconds has elapsed.

In some embodiments, instead of a single target being used, dual targets (a Negative Target and a Positive Target) may be used. It is important to note that the terms "negative" and "positive" relating to the targets as used herein do not necessarily mean that the target values are negative or positive, and instead are used to refer to the target(s) on which the negative pressure support and positive pressure support are based. The Negative Target and the Positive Target may have different values. When the measure of flow exceeds the Negative Target, the pressure support to be delivered to the patient may be modified by reducing the baseline pressure support level by the negative pressure support level. In embodiments where a Positive Target is used, if the measure of flow is below the Positive Target, the pressure support to be delivered to the patient may be modified by adding the positive pressure support level to the baseline pressure support level. In some embodiments, a single Target may be used for the Positive Target and the Negative Target. In other words, the Positive Target and the Negative Target may be the same.

Figure 8:
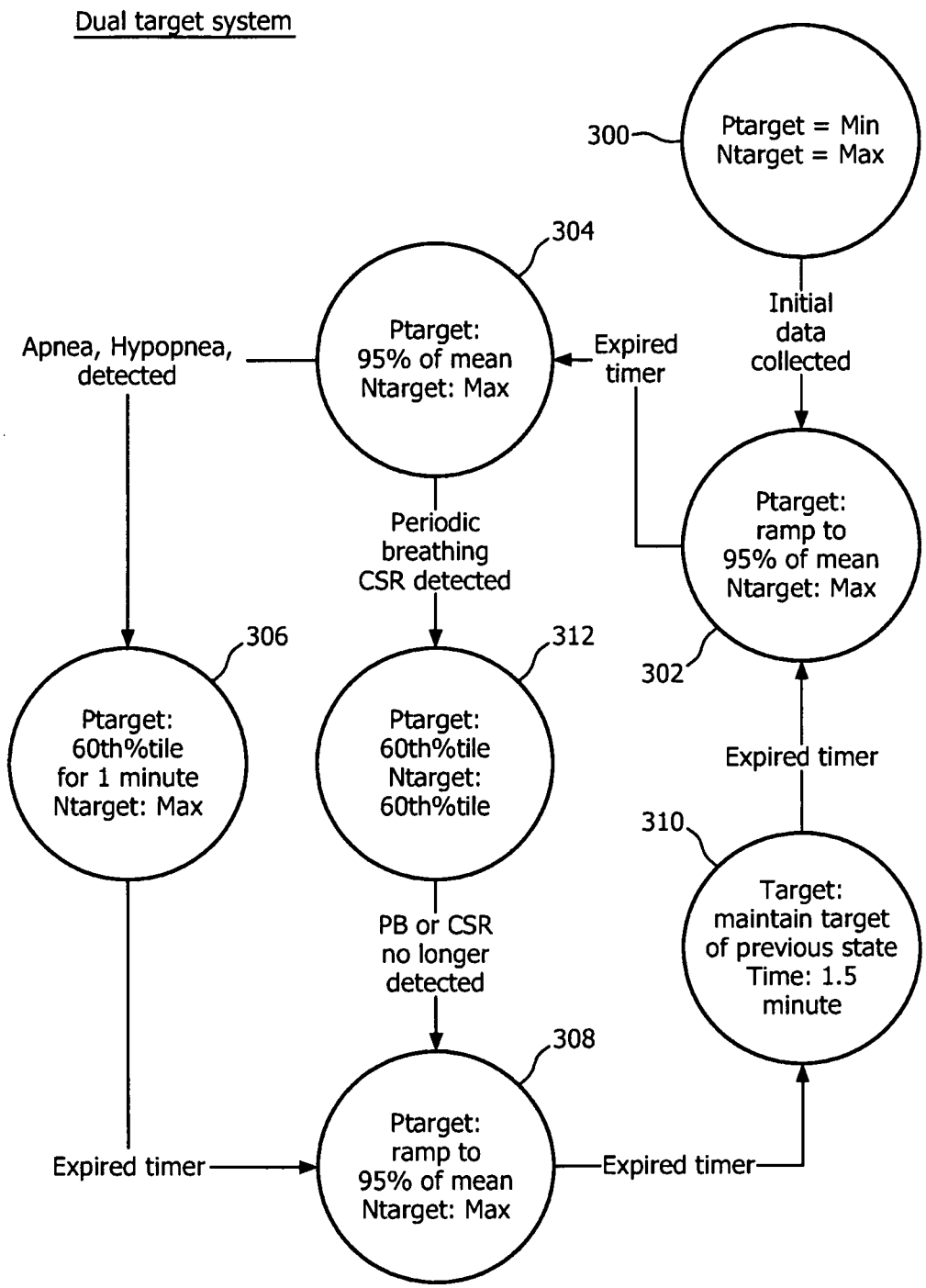
FIG. 8 is a state diagram explaining the dual Target selection process in accordance with an embodiment.

FIG. 8 is a state diagram showing, in detail, the process for selecting the statistical measures to be used as the dual Targets (the Negative Target and the Positive Target). When the pressure support system 10 is actuated, the Negative and Positive Target selection process starts at step 300, where the Positive Target is set to a minimum value, the Negative Target is set to a maximum value, and initial data is collected. In an embodiment, the minimum and maximum values for the Negative Target and the Positive Target are determined empirically. In some embodiments, this minimum Target is set to 15 lpm. In some embodiments, the maximum Target is set to 50 lpm. It is to be understood, however, that the present invention contemplates that the Negative Target and Positive Target can be set by the system based on monitored physiological characteristics of the patient, such as whether the patient is deemed to be experiencing sleep disordered breathing, flow limitations, etc.

In step 302, the Positive Target is increased to a value that corresponds to 95% of the mean value of the measure of flow data thus collected. In an embodiment, the increase in the Target is done in a linear, ramp fashion over a period of time that spans several respiratory cycles, such as 30 seconds. This ramp in the Target is done to avoid rapid pressure fluctuations being introduced to the patient, thereby optimizing patient comfort and compliance with the treatment. The shape or pattern for the change (ramp) in the Target can be done at a fixed rate, so that the ramp is linear. It can also be done at non-linear rates, so that the ramp shape is not linear. In an embodiment, ramp in Target takes place at a rate of 0.5 lpm per breath. The Negative Target is maintained at the maximum value. In some embodiments, this setting for the Negative Target essentially disables negative target support. As mentioned above, the baseline positive pressure support to be delivered to the patient is reduced by the negative pressure support when the measure of flow exceeds the Target. In embodiments having dual Targets, negative pressure support is reduced from the baseline positive pressure support when the measure of flow exceeds the Negative Target. As such, if the Negative Target is set to a high value, the measure of flow might not be able to exceed the Negative Target criteria for the negative pressure support to be reduced from the baseline positive pressure support.

In step 304, the Positive Target value is maintained at the value that corresponds to 95% of the mean value of the measure of flow. The Negative Target is maintained at the maximum value.

If, however, a sleep disordered breathing event, such as an apnea or hypopnea, is detected the process moves to step 306, where the Target is changed to the 60th percentile. This increase in the Target provides a greater likelihood that the system will increase the pressure support, and, thus treat the sleep disordered breathing event, than if the Target is not changed. At this step, the Negative Target is still maintained at the maximum level. As mentioned above, in some embodiments, this setting for the Negative Target essentially disables negative pressure support. The Positive Target and the Negative Target are maintained at this level for a period of time, such as one minute. After that, the process moves to step 308.

In step 308, the Positive Target is changed back to the 95% of the mean value of the measure of flow data currently collected. In an embodiment, this change takes place in a linear, ramp fashion, over a period of time that spans several respiratory cycles, such as 2 minutes at a rate of 0.5 lpm per breath. The change in Positive Target can also be done at a non-linear rate. The Negative Target is maintained at the maximum value.

The system maintains the Positive Target and the Negative Target at its current value in a hold state in step 310. As mentioned above, this is done to allow the patient to stabilize under the new value for the Positive and Negative Targets. This prevents the system of the present invention from overcompensating or being too aggressive in its reactions to the monitored condition of the patient. In an embodiment, this hold state lasts for 1.5 minutes. Other periods of time may optionally be used, and this period of time can be selected dynamically by the system. After the 1.5 minute hold, the process returns to step 302.

If a CSR event or periodic breathing is detected during step 304, the process moves to step 312, where the Positive Target is changed to the 60th percentile. The Negative Target is changed to the 65 percentile. At this step 312, if the measure of flow exceeds the Negative Target, then the baseline positive pressure support is reduced by the negative pressure support so that a modified pressure support is delivered to the patient. The Positive and Negative Targets are maintained at this level for a relatively short period of time, such as 30 seconds. If no CSR events are detected during this 30 second window, the process moves to step 308. If, however, CSR events continue to be detected, the system will continue to hold the timer in reset and the process will remain in step 312. The process proceeds to step 308 when periodic breathing or CSR is no longer detected and the 30 seconds has elapsed.

It can be appreciated that the embodiments are not to be limited to the specific time periods, percentages, and constants noted above. Rather, other values for these quantities can be used so long as the general principles of the present invention are maintained. In addition, these quantities need not be fixed. Instead, they can be dynamically altered by the controller based on the monitored condition of the patient. This can be done, for example, to treat the patient more aggressively if they are not responding to the current treatment scheme, and vise versa.

Controller 64 determines the amount of pressure that must be provided to the patient to eliminate or reduce CSR. As noted above, in some embodiments, either one or both of inspiratory pressure and expiratory pressure levels may be varied by the controller. In some embodiments, one of inspiratory pressure or expiratory pressure may be manually set or pre-established, and the other of the inspiratory pressure or expiratory pressure levels may be varied by controller 64.

Referring back to FIG. 5, in step 250, system 10 determines the pressure support to be delivered to the patient. That is, the system determines whether the pressure support level delivered to the patient should be modified from the baseline pressure support level.

In some embodiments, the inspiratory/expiratory pressure to be delivered to the patient in step 250 may be determined based on 1) the current measure of flow, such as the $Q_{ave}$(max) in some embodiments, 2) the pressure support delivered during the previous breath, 3) the Target value determined in step 150, and 4) a gain factor. As noted above, the pressure support is the difference between the inspiratory pressure level and the expiratory pressure level.

In some embodiments, the following algorithm may be used to determine the change in pressure support to be delivered to a patient during a current breath (k+1):

$$PS(k+1)=PS(k)+Gain*(Target-Q_{ave}(max)(k)) \quad 1.3$$

where k is the index of the last breath, PS(k) is the pressure support delivered during the previous breath, Gain is a factor that converts flow into pressure, Target is determined as discussed above, and $Q_{ave}$(max) (k) is the Maximum Average Inspiratory Flow $Q_{ave}$(max) from the previous breath. In some embodiments, the Gain factor may be a 30 breath average of a ratio of pressure support (PS) over the Maximum Average Inspiratory Flow, as described in U.S. patent application Ser. No. 11/235,520, which is incorporated herein in its entirety.

It is important to note that the use of $Q_{ave}$(max) in Eq. 1.3 as the measure of flow is not intended to be limiting. Other measures of flow may be used, just for example, tidal volume, minute ventilation, or mean flow. Thus, mean flow, minute ventilation, or tidal volume may be compared against a target mean flow, target minute ventilation, or a target tidal volume.

In some embodiments, the measure of flow, such as, for example, $Q_{ave}$(max), is constantly compared against the Target(s). In embodiments that use the moving target process shown in FIG. 7, whenever the measure of flow exceeds the Target, the negative pressure support level is calculated, such as for example, according to Eq. 1.3 The baseline pressure support level is then reduced by the calculated negative pressure support level to achieve the modified pressure support level. Thus, in embodiments that vary the inspiratory pressure level, the inspiratory pressure level may be reduced as a result. In some embodiments, because a baseline pressure support level is already being provided to the patient, when the calculated negative pressure support level is small, the modified pressure support may still be a positive pressure support. That is, the modified pressure support level may still have an inspiratory pressure that is above the expiratory pressure. However, in some embodiments, if the negative pressure support level is large, the modified pressure support level delivered to the patient may become negative. That is, the inspiratory pressure level may become lower than the expiratory pressure level. In some embodiments, system 10 may allow this only during certain events, such as, for example, when CSR has been detected. To accommodate a patient's comfort, system 10 may optionally prevent negative pressure support from being delivered when the patient has been aroused from sleep. It is also contemplated that the system may only allow the modified pressure support to become negative pressure support during certain phases, such as only during the hyperpneic phase of either CSR or repetitive hypopnea or apnea. In some embodiments, the baseline positive pressure support may only be modified when certain events, such as CSR or other sleep disorder breathing events, have been detected.

As mentioned above, some embodiments use dual targets. In such embodiments, when the measure of flow is below the Positive Target, the pressure support provided to the patient is modified by adding a positive pressure support level to the baseline support level. The positive pressure support level may be calculated according to Eq. 1.3.

It is worth noting that because the pressure support being delivered to the patient may be modified by reducing the baseline pressure support level when the measure of flow exceeds the Target or the Negative Target, system 10 maintains the measure of flow below the Target or the Negative Target. That is, the Target or the Negative Target functions essentially as a "ceiling." In contrast, when positive pressure support is provided, the system maintains the measure of flow above the Positive Target, and the Positive Target functions as a "floor."

The process shown in FIG. 5 shows the calculations that are performed by the pressure support system 10 during each breath. Controller 64 may determine whether to modify the pressure support being provided to the patient. That is, the controller may determine whether to add a positive pressure support level to the baseline pressure support level or reduce the baseline pressure support level by a negative pressure support level. If the measure of flow is above the Target or the Negative Target, the pressure support provided to the patient is modified by reducing the baseline pressure support level by a negative pressure support level. In embodiments that use a Positive Target, if the measure of flow is below the Positive Target, the pressure support provided to the patient is modified by adding a positive pressure support level to the baseline pressure support level. The pressure support system 10 may deliver pressure support using the methods described in U.S. patent application Ser. No. 11/235,520 and U.S. Pat. No. 7,267,122, which are incorporated herein in its entirety. Controller 64 may determine whether it is in the inspiratory phase of the respiratory cycle. This may be accomplished using any conventional technique for differentiating between inspiration and expiration. In an embodiment, a flag is set whenever the patient is in inspiration. A flag may also be set whenever the patient is in expiration.

In embodiments where a flag is set during inspiration, if the patient is in the inspiratory phase of the respiratory cycle, the controller causes the gas flow/pressure generator to begin to deliver the inspiratory pressure $P_{insp}$ to the patient based on the modified pressure support level. Controller 64 may then control the pressure delivered to the patient during or within the respiratory cycle. The controller determines whether the pressure support delivered to the patient is sufficient. In some embodiments, the modified pressure support delivered thus far is considered to be sufficient if the modified pressure support delivered by system 10 under the current magnitude and rate of decrease will result in $Q_{ave}$(t) meeting or being slightly below the Target. In some embodiments, controller 64 may deliver pressure support and determine if the pressure support delivered is sufficient, as described in U.S. patent application Ser. No. 11/235,520, and/or U.S. Pat. No. 7,267,122, which are hereby incorporated by reference in its entirety.

Controller 64 may implement any of the standard functions of a pressure support device, i.e., providing CPAP, bi-level pressure support BiPAP, PPAP pressure support, smart-CPAP as taught, for example, in U.S. Pat. Nos. 5,203,343; 5,458,137; and 6,087,747, the contents of which are incorporated herein by reference, or auto-titration CPAP as taught, for example, in U.S. Pat. No. 5,645,053, the contents of which are also incorporated herein by reference, in addition to implementing the CSR treatment mode of pressure support as disclosed herein. In one embodiment, the pressure support system 10 includes a mode select input device that allows a user or authorized caregiver to select the mode of ventilation (CSR treatment technique, CPAP, bi-level, auto-titration CPAP, PAV, PPAP, etc.) under which the pressure support device operates. In addition, CSR detection techniques may be performed in the background while implementing a conventional mode of pressure support and then switching to the CSR treatment mode of pressure support once CSR is detected.

Although the invention has been described in detail for the purpose of illustration based on what is currently considered to be the most practical embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is contemplated that, to the extent possible, one or more features of any embodiment can be combined with one or more features of any other embodiment.

What is claimed is:

1. A system for delivering a flow of breathing gas to an airway of a patient, the system comprising:
    a gas flow generator configured to generate the flow of gas;
    a patient circuit coupled to the gas flow generator configured to communicate the flow of gas to an airway of the patient;
    a sensor configured to generate output signals related to one or more parameters associated with the flow of gas; and
    a controller configured to:
        control the flow of breathing gas to the airway of the patient via the patient circuit,
        provide an inspiratory pressure level during inspiration and an expiratory pressure level during expiration, and
        determine the inspiratory pressure level and the expiratory pressure level based on the one or more parameters associated with the flow of gas such that, responsive to the one or more parameters indicating a hyperneic phase of Cheyne-Stokes Respiration, the expiratory pressure level becomes greater than the inspiratory pressure level.

2. The system of claim 1, wherein the controller determines whether the patient is experiencing a predetermined breathing characteristic based on the one or more parameters associated with the flow of gas, and wherein the controller alters the inspiratory pressure level, the expiratory pressure level, and/or both based on a determination that the patient is experiencing the predetermined breathing characteristic.

3. The system of claim 2, wherein the predetermined breathing characteristic is a sleep disorder breathing event comprising one or more of Cheyne-Stokes Respiration, hypopnea, or apnea.

4. The system of claim 2, wherein the predetermined breathing characteristic is Cheyne-Stokes Respiration, further comprising an oxygen saturation monitor configured to generate output signals related to an oxygen saturation of the patient, and wherein the controller determines whether the patient is experiencing Cheyne-Stokes Respiration based, at least in part, on an output of the oxygen saturation monitor.

5. The system of claim 1, wherein the one or more parameters associated with the flow of gas comprises a flow rate.

6. The system of claim 1, wherein the one or more parameters associated with the flow of gas comprises a Maximum Average Inspiratory Flow ($Q_{ave}(max)$).

7. The system of claim 1, wherein the one or more parameters associated with the flow of gas comprises a tidal volume.

8. The system of claim 1, wherein the one or more parameters associated with the flow of gas comprises a minute ventilation.

9. A method of ventilating a patient, comprising:
    delivering a flow of gas to an airway of a patient from a source of breathing gas via a patient circuit;
    measuring a first characteristic associated with the flow of gas;
    determining a target of the flow of gas to be delivered to the patient; and
    controlling the delivery of the flow of gas to the airway of the patient from a gas flow generator via the patient circuit by:
        1) delivering the flow of gas to the airway of the patient at an inspiratory pressure level during inspiration and an expiratory pressure level during expiration,
        2) determining the inspiratory pressure level and the expiratory pressure level based on the first characteristic associated with the flow of gas, and
        3) controlling the flow of gas such that the expiratory pressure level is greater than the inspiratory pressure level responsive to the first characteristic indicating a hyperneic phase of Cheyne-Stokes Respiration.

10. The method of claim 9, wherein controlling the delivery of the flow of gas to the airway of the patient comprises maintaining the flow of gas below the target.

11. The method of claim 9, further comprising determining whether the patient is experiencing a predetermined breathing characteristic based on the measured first characteristic and altering the target based on a determination that such a patient is experiencing the predetermined breathing characteristic.

12. The method of claim 11, wherein the predetermined breathing characteristic is a sleep disorder breathing event.

13. The method of claim 12, wherein the sleep disorder breathing event is Cheyne-Stokes Respiration, hypopnea, or apnea.

14. The method of claim 9, wherein the first characteristic is a flow rate.

15. The method of claim 9, further comprising outputting a signal indicative of an oxygen saturation of the patient, and wherein the signal is used to determine whether the patient is experiencing Cheyne-Stokes Respiration.

16. The method of claim 9, wherein the first characteristic is a Maximum Average Inspiratory Flow ($Q_{ave}(max)$), a tidal volume, or a minute ventilation.

17. A system for ventilating a patient, comprising:
  means to generate a flow of gas;
  means to deliver a flow of gas to an airway of a patient from the means to generate the flow of gas;
  means to generate output signals related to one or more parameters associated with the flow of gas;
  means to control the flow of breathing gas to the airway of the patient via the patient circuit;
  means to provide an inspiratory pressure level during inspiration and an expiratory pressure level during expiration; and
  means to determine the inspiratory pressure level and the expiratory pressure level based on the one or more parameters associated with the flow of gas such that, responsive to the one or more parameters indicating a hyperneic phase of Cheyne-Stokes Respiration, the expiratory pressure level is greater than the inspiratory pressure level.

18. The system of claim 17, wherein the means to control the flow of gas to the airway of a patient determines, based on the one or more parameters associated with the flow of gas, whether the patient is experiencing a predetermined breathing characteristic, and wherein the means to control alters the inspiratory pressure level, the expiratory pressure level, and/or both based on a determination that the patient is experiencing the predetermined breathing characteristic.

19. The system of claim 18, wherein the predetermined breathing characteristic is a sleep disorder breathing event, Cheyne-Stokes Respiration, hypopnea, or apnea.

20. The system of claim 18, wherein the predetermined breathing characteristic is Cheyne-Stokes Respiration, further comprising means to output a signal indicative of an oxygen saturation of the patient, and wherein the means to control flow determines whether the patient is experiencing Cheyne-Stokes Respiration based, at least in part, on an output of the means to output a signal indicative of oxygen saturation.

21. The system of claim 17, wherein the one or more parameters associated with the flow of gas comprises a flow rate.

22. The system of claim 17, wherein the one or more parameters associated with the flow of gas comprises a Maximum Average Inspiratory Flow ($Q_{ave}(max)$).

23. The system of claim 17, wherein the one or more parameters associated with the flow of gas comprises a tidal volume.

* * * * *